United States Patent [19]

Wilk

[11] Patent Number: 5,254,113
[45] Date of Patent: Oct. 19, 1993

[54] ANASTOMOSIS METHOD

[76] Inventor: Peter J. Wilk, 185 West End Ave., New York, N.Y. 10023

[21] Appl. No.: 937,598

[22] Filed: Aug. 31, 1992

[51] Int. Cl.$^5$ ............................................. A61B 17/36
[52] U.S. Cl. .................................... 606/8; 606/148; 606/150; 606/153; 606/154; 606/195; 606/213; 606/214; 623/12; 128/898
[58] Field of Search ................. 606/8, 108, 148, 150, 606/151, 153, 154–156, 195, 213–215; 623/12; 128/898

[56] References Cited

U.S. PATENT DOCUMENTS

| | | | |
|---|---|---|---|
| 2,127,903 | 8/1938 | Bowen | 606/154 |
| 2,453,056 | 11/1948 | Zack | 606/153 |
| 4,470,415 | 9/1984 | Wozniak | 606/153 |
| 4,520,823 | 6/1985 | LeVeen et al. | 606/195 |
| 4,586,504 | 5/1986 | Medinaceli | 606/155 |
| 4,625,724 | 12/1986 | Suzuki et al. | 606/8 |
| 4,690,684 | 9/1987 | McGreevy et al. | 606/154 |
| 4,762,127 | 8/1988 | Narayanan et al. | 606/156 |
| 4,917,087 | 4/1990 | Walsh et al. | 606/153 |
| 5,037,428 | 8/1991 | Picha et al. | 606/148 |
| 5,156,613 | 10/1992 | Sawyer | 606/8 |

FOREIGN PATENT DOCUMENTS

| | | | |
|---|---|---|---|
| 0237021 | 9/1987 | European Pat. Off. | 606/156 |
| 1169625 | 7/1985 | U.S.S.R. | 606/153 |

Primary Examiner—Stephen C. Pellegrino
Assistant Examiner—Jeffrey A. Schmidt
Attorney, Agent, or Firm—R. Neil Sudol; Henry D. Coleman

[57] ABSTRACT

A method for use in performing an anastomosis includes the steps of juxtaposing free ends of two sections of a ressected tubular organ of a patient so as to form a continuous lumen through the sections, placing a strip of a biocompatible material over the sections along a seam therebetween, and bonding the strip to outer surfaces of the sections so as to form a seal about the sections at the seam. The juxtaposition of the organ sections is facilitated by inserting an inflatable balloon made of bioabsorbable material into the sections at their free ends, inflating the ballon and pulling the sections over the inflated balloon.

19 Claims, 2 Drawing Sheets

ANASTOMOSIS METHOD

BACKGROUND OF THE INVENTION

This invention relates to a method for use in performing an anastomosis.

Upon removing a diseased, injured or otherwise disfunctioning segment of a tubular organ from a patient in a ressection operation, the free ends of the remaining segments must be connected to one another to form a continuous lumen through the organ to thereby restore functioning of the organ. Generally, there are two methods for connecting a ressected intestine. One method is an end-to-end anastomosis wherein the circular edges of the free ends are juxtaposed to one another and the organ segments stapled or sutured to one another. Another method includes the steps of juxtaposing lateral walls of the organ segments, cutting co-extensive openings in the overlapped organ segments walls, connecting the overlapped organ segment walls along the edges of the openings, and closing the free ends of the organ segments. The connection and closure operations are generally implemented via stapling.

In anastomoses the problem of leakage frequently arises. Attempts to overcome the leakage have given rise to a laser bonding technique wherein laser beams of relatively low energy are used to bond justaposed tissues to one another.

OBJECTS OF THE INVENTION

An object of the present invention is to provide a method for use in performing an anastomosis which serves to reduce leakage at a seam between two connected organ sections.

Another object of the present invention is to provide such a method which is easy and straightforward.

Another, more particular, object of the present invention is to provide such a method which can be used in conjunction with conventional techniques for connecting ressected organ segments.

A further object of the present invention is to provide a method for facilitating the positioning of organ segments during an anastomosis operation.

Yet another object of the present invention is to provide a new technique for forming an anastomosis.

These and other objects of the present invention will be apparent from the drawings and detailed descriptions herein.

SUMMARY OF THE INVENTION

A method for use in performing an anastomosis comprises, in accordance with the present invention, the steps of (a) juxtaposing free ends of two sections of a ressected tubular organ of a patient so as to form a continuous lumen through the sections, (b) placing a strip of a biocompatible material over the sections along a seam therebetween, and (c) bonding the strip to outer surfaces of the sections so as to form a seal about the sections at the seam.

According to another feature of the present invention, the juxtaposition of the organ sections is facilitated or implemented by inserting an inflatable balloon into the sections at their free ends and inflating the balloon. Preferably, the balloon is made of a bioabsorbable (e.g., proteinaceous) material. The balloon remains in the repaired organ upon completion of the anastomosis and is absorbed by the body within hours. However, in the event that the subject organ is a bowel, the balloon may be made of a non-bioabsorbable material. In that event, the balloon is deflated at or near the completion of the operation and is subsequently flushed out of the body during defecation.

A tubular inflation member is connected to the balloon for pressurizing the balloon during the inflation step. The method then further comprises the step of severing the tubular member upon inflation of the balloon. In the event that the balloon is made of bioabsorbable material, the balloon may remain inflated upon the severing of the tubular member. In that event, the tubular member is sealed.

According to another feature of the present invention, the balloon is in the form of a cylinder. This form of the balloon facilitates normal operation of the ressected organ prior to absorption of the balloon by the body.

According to a specific embodiment of of the present invention, the step of juxtaposing includes the step of inserting a free end of one of the organ sections into the free end of the other organ section. In that event, the method may additionally comprise the step of separating a mucosal lining from a muscular wall of the outer section in an annular region about the free end that section prior to the insertion of the inner organ section into the outer section. In this embodiment of the invention, the two organ sections may be connected (e.g., stapled, sutured) at their free ends to one another prior to the placement and bonding of the sealing strip. Alternatively, the connection between the two organ sections is made by the sealing strip.

Pursuant to another feature of the present invention, the organ sections may be connected to one another along the seam, e.g., by stapling or suturing, prior to the placement of the sealing strip over the seam.

Preferably, the sealing strip is made of a bioabsorbable material such as a proteinaceous material.

Pursuant to another feature of the present invention, the bonding of the sealing strip to the organ sections is implemented via laser welding. Alternatively or additionally, a biocompatible adhesive may be used.

A method for use in performing an anastomosis comprises, in accordance with a particular embodiment of the present invention, the steps of (i) inserting an inflatable balloon into free ends of two sections of a ressected tubular organ of a patient, (ii) inflating the balloon, (iii) juxtaposing the free ends of the organ sections over the inflated balloon, and (iv) connecting the two organ sections at their free ends to one another so as to form a continuous lumen through the connected sections.

As discussed hereinabove, where a tubular inflation member is connected to the balloon for pressurizing same during the step of inflating, the method further comprises the step of severing the tubular member upon inflation of the balloon.

A method for use in performing an anastomosis comprises, in accordance with another particular embodiment of the present invention, the steps of (1) inserting a free end of a first section of a ressected tubular organ of a patient into a free end of a second section of the ressected tubular organ so as to form a continuous lumen through the connected sections, and (2) connecting the first section to the second section along overlapping portions of the first section and the second section.

In accordance with another feature of this embodiment, the method further comprises the step of separating a mucosal lining from a muscular wall of the second section in an annular region about the free end of the second section prior to the insertion of the first organ section into the second organ section.

The step of connecting in this embodiment may include the steps of placing a strip of a biocompatible material over the sections along a seam therebetween and bonding the strip to outer surfaces of the sections so as to form a seal about the seam.

In accordance with a further feature of this embodiment, the method also comprises the step of connecting the two sections at their free ends to one another prior to the steps of placing and bonding.

In an anastomosis operation, use of a sealing strip in accordance with the present invention serves to reduce leakage at a seam between two connected organ sections. The method is easy and straightforward and can be used in conjunction with conventional techniques for connecting ressected organ segments.

A method in accordance with the present invention also serves to facilitates the positioning of organ segments during an anastomosis operation.

DETAILED DESCRIPTION

Figure 1A:
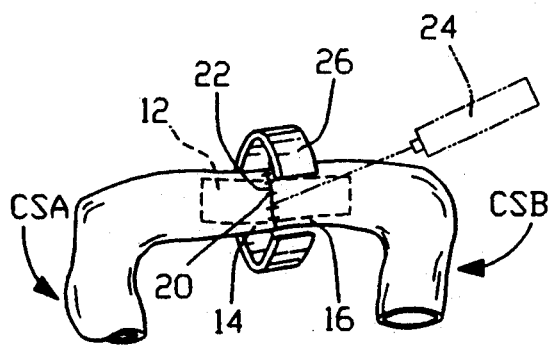
FIGS. 1A and 1B are schematic perspective views showing successive steps in an anastomosis operation in accordance with the present invention.

As illustrated in FIG. 1A, in performing an anastomosis, for example, connecting two sections or segments CSA and CSB of a ressected colon, a stent 12 is placed inside free ends 14 and 16 of colon segments CSA and CSB. The free ends 14 and 16 are pulled over stent 12 until the roughly circular edges of the free ends are juxtaposed. Sutures or staples 20 are then inserted through the tissues of free organ ends 14 and 16 to connected colon segments CSA and CSB to one another along a seam 22. Alternatively, free ends 14 and 16 may be bonded or organically welded to one another via the use of a low-power Nd:YAG laser 24.

The juxtaposition of free ends 14 and 16 results in a continuous lumen being formed through colon segments CSA and CSB.

Figure 1B:
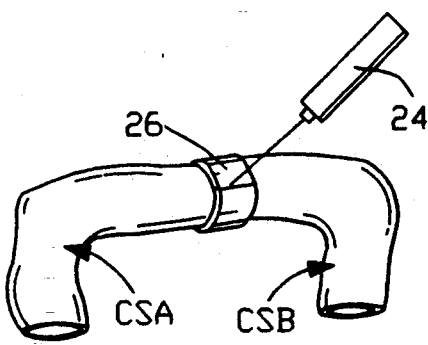

As illustrated in FIGS. 1A and 1B, upon the connection of colon segments CSA and CSB to one another at their free ends 14 and 16, a strip 26 of a bioabsorbable material is wrapped around segments CSA and CSB to cover free ends 14 and 16 and seam 22. Strip 26 is then bonded to outer surfaces of colon segments CSA and CSB so as to form a seal about the segments at seam 22. FIG. 1B depicts the bonding step as being implemented via low-power laser 24. Alternatively, or additionally, a biocompatible adhesive such as cyanoacrylate may be used to bond the strip to the muscular walls of segments CSA and CSB.

Figure 2A:
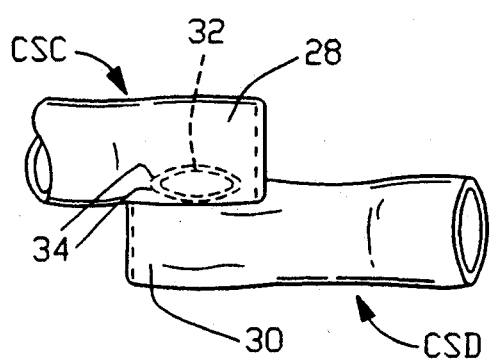
FIGS. 2A and 2B are schematic perspective views depicting consecutive steps in another anastomosis operation in accordance with the present invention.

FIG. 2A illustrates a conventional anastomosis wherein free ends 28 and 30 of colon sections CSC and CSD are laterally juxtaposed to one another. Co-extensive openings 32 are then cut in the overlapped walls of organ sections CSC and CSD and the overlapped walls of organ sections CSC and CSD are connected along the edges of openings 32, e.g., via staples or sutures 34. Free ends 28 and 30 of organ sections CSC and CSD are closed via suturing, stapling or laser welding.

Figure 2B:
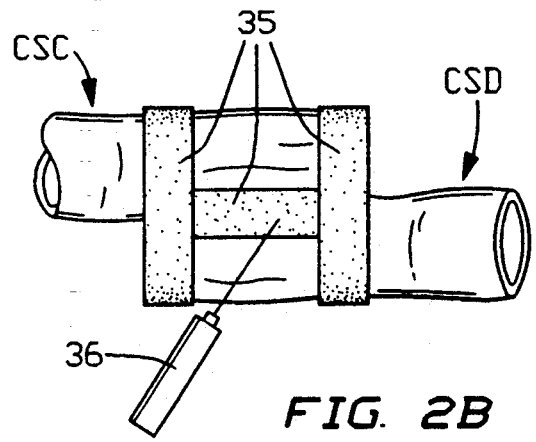

As shown in FIG. 2B, strips 35 of a bioabsorbable material are placed over the seams or joints between colon sections CSC and CSD and are joined to the outer walls of the colon sections by use of a low-power laser 36 and/or adhesive.

Figure 3A:
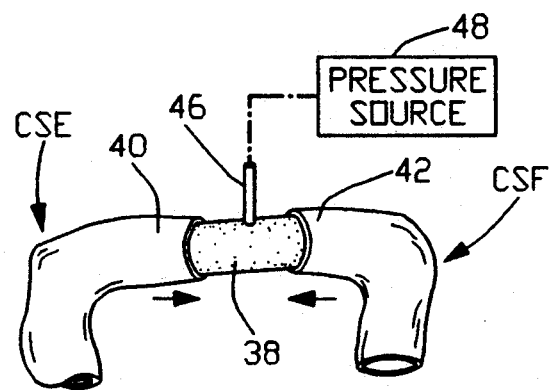
FIGS. 3A-3C are schematic perspective views illustrating successive steps in a further anastomosis operation in accordance with the present invention.
Figure 3B:
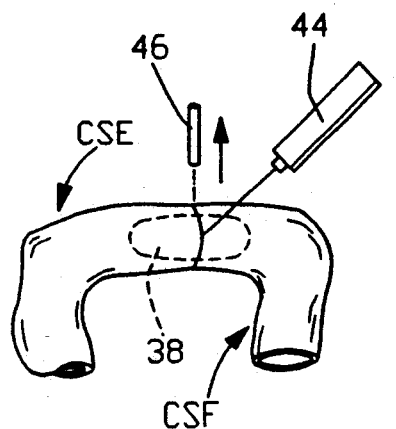

As depicted in FIG. 3A, in another anastomosis operation, an inflatable balloon 38 is inserted into colon sections CSF and CSE at their free ends 40 and 42. Balloon 38 is then inflated and free ends 40 and 42 are pulled over the balloon to juxtapose the free ends, as depicted in FIG. 3B. Subsequently, colon sectiosn CSE and CSF are joined at their juxtaposed ends 40 and 42, for example, through the use of a welding laser 44.

Balloon 38 is made of a bioabsorbable (e.g., proteinaceous) material. Balloon 38 remains in the repaired organ upon completion of the anastomosis and is absorbed by the body within hours.

As illustrated in FIG. 3A, a tubular inflation member 46 is connected to balloon 38 for pressurizing the balloon with air from a source 48. As illustrated in FIG. 3B, tubular member 46 is severed upon inflation of balloon 38. Tubular member 46 may be sealed (e.g., via a pressure weld or a biocompatible adhesive), whereupon balloon 38 remains inflated upon the severing of tubular memebr 46.

Figure 3C:
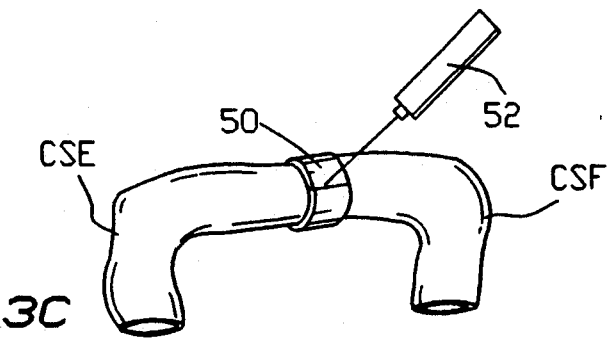

As shown in FIG. 3C, a strip 50 of bioabsorbable material is wrapped around colon segments CSE and CSF and bonded thereto, e.g., via a laser 52.

Figure 4:
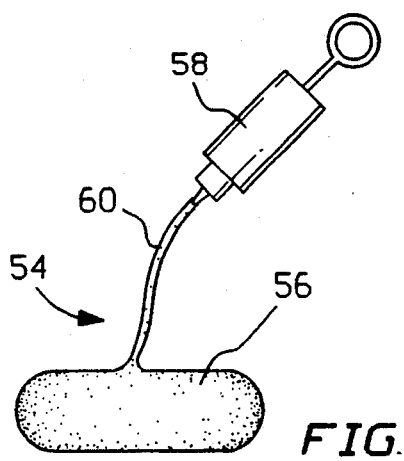
FIG. 4 is a schematic perspective view of a device utilizable in the anastomosis operation of FIGS. 3A-3C.
Figure 5:
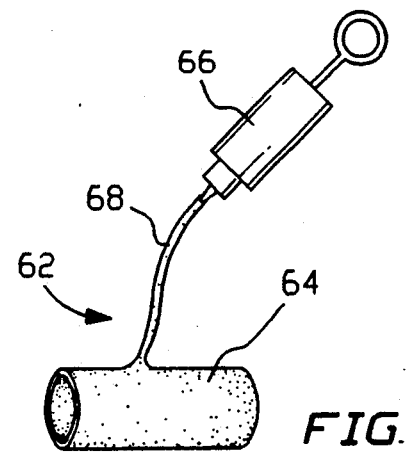
FIG. 5 is a schematic perspective view of another device utilizable in the anastomosis operation of FIGS. 3A-3C.

FIG. 4 shows a device 54 utilizable in the anastomosis operation of FIGS. 3A-3C. Device 54 includes a substantially cylindrical balloon 56 made of a bioabsorbable material connected to a syringe 58 via a tubular inflation element 60. FIG. 5 shows another device 62 utilizable in the anastomosis operation of FIGS. 3A-3C. Device 62 incorporates a cylindrical balloon 64 made of a bioabsorbable material. Balloon 64 is coupled to a pressure source in the form of a syringe 66 via a tubular inflation element 68. Cylindrical balloon 64 facilitates normal operation of the ressected organ prior to absorption of the balloon by the body.

Figure 6A:
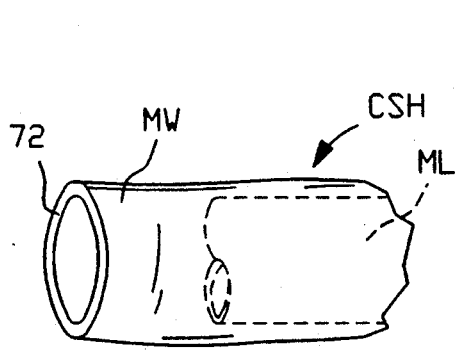
FIGS. 6A-6C are schematic perspective views illustrating successive stages of yet another anastomosis operation in accordance with the present invention.
Figure 6B:
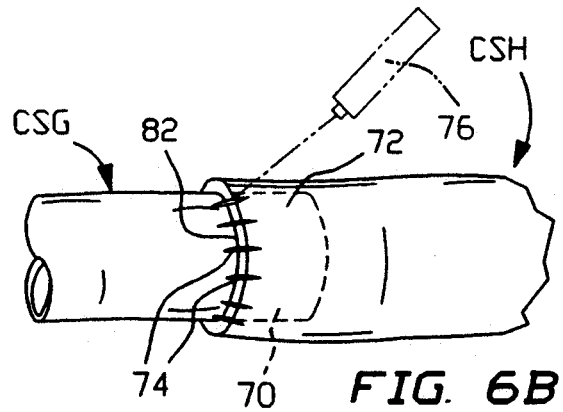
Figure 6C:
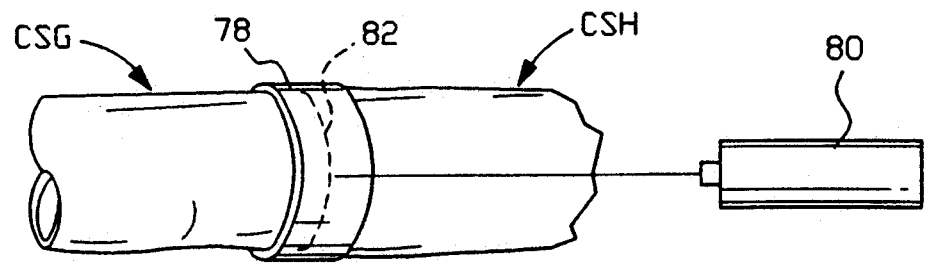

In another anastomosis operation depicted schematically in FIGS. 6A-6C, a free end 70 of one tubular organ section CSG is inserted into a free end 72 of another organ section CSH, as shown in FIG. 6B. Prior to that insertion, a mucosal lining ML of the outer organ segment CSH is cut and removed from an outer muscular wall MW in an annular region about free end 72. Organ sections CSG and CSH may be connected to one another at their free ends 70 and 72 by sutures or staples 74 or by a laser 76 (FIG. 6B) prior to placement and bonding of a sealing strip 78 (FIG. 6C). Alternatively, the connection between organ sections CSG and CSH is made by the sealing strip 78. In the later event, staples or sutures 74 are omitted. Strip 78 is bonded to organ sections CSG and CSH via a laser 80 and seals a seam 82 against leakage.

Sealing strips 26, 35, 50 and 78 are preferably made of a bioabsorbable material which is absorbed more slowly into the body than the material of balloons 38, 56, 64. The absorption of the strips 26, 35, 50 and 78 is timed so that an anastomosis seam is closed by the time that the covering strip is absorbed. Accordingly, the possibility of leakage is minimized.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A method for use in performing an anastomosis, comprising the steps of:

juxtaposing free ends of two sections of a ressected tubular organ of a patient so as to form a continuous lumen through the sections upon termination of a connection operation, said step of juxtaposing including the steps of inserting an inflatable balloon into said sections at their free ends, inflating said balloon, and pulling said sections over the inflated balloon;

placing a strip of a biocompatible material over said sections along a seam therebetween; and bonding said strip to outer surfaces of said sections so as to form a seal about said seam.

2. The method defined in claim 1 wherein a tubular inflation member is connected to said balloon for pressurizing same during said step of inflating, further comprising the step of severing said tubular member upon completion of said step of inflating.

3. The method defined in claim 1 wherein said balloon is in the form of a cylinder.

4. The method defined in claim 1 wherein said balloon is made of bioabsorbable material.

5. The method defined in claim 1 wherein said step of juxtaposing includes the step of inserting a free end of one of said sections into the free end of the other of said sections.

6. The method defined in claim 5, further comprising the step of separating a mucosal lining from a muscular wall of said other of said sections in an annular region about the free end of said other of said sections prior to said step of inserting.

7. The method defined in claim 5, further comprising the step of connecting said two sections to one another in a region about their free ends prior to said steps of placing and bonding.

8. The method defined in claim 1, further comprising the step of connecting said two sections at their free ends to one another so as to form a continuous lumen through the connected sections prior to said steps of placing and bonding.

9. The method defined in claim 8 wherein said step of connecting includes the step of suturing said sections to one another along said seam.

10. The method defined in claim 8 wherein said step of connecting includes the step of stapling said sections to one another along said seam.

11. The method defined in claim 1 wherein said strip is made of a bio-absorbable material, further comprising the steps of leaving said balloon in said lumen upon completion of said step of connecting and gradually absorbing the material of said balloon into tissues of the organ.

12. The method defined in claim 1 wherein said step of bonding includes the step of laser welding said strip to said outer surfaces.

13. The method defined in claim 1 wherein said step of bonding includes the step of glueing said strip to said outer surfaces with a biocompatible adhesive.

14. The method defined in claim 1 wherein said seam is circular and said step of placing includes the step of shaping said strip into a substantially cylindrical form.

15. A method for use in performing an anastomosis, comprising the steps of:

inserting an inflatable balloon into free ends of two sections of a ressected tubular organ of a patient;

inflating said balloon;

juxtaposing said free ends of said sections over the inflated balloon; and connecting said two sections at their free ends to one another so as to form a continuous lumen through the connected sections.

16. The method defined in claim 15 wherein a tubular inflation member is connected to said balloon for pressurizing said balloon during said step of inflating, further comprising the step of severing said tubular member upon completion of said step of inflating.

17. The method defined in claim 15 wherein said step of inflating includes the step of expanding said balloon to the form of a cylinder.

18. The method defined in claim 15 wherein said balloon is made of bioabsorbable material, further comprising the steps of leaving said balloon in said lumen upon completion of said step of connecting and gradually absorbing the material of said balloon into tissues of the organ.

19. The method defined in claim 15 wherein said step of connecting includes the steps of placing a strip of a biocompatible material over said sections along a seam therebetween and bonding said strip to outer surfaces of said sections so as to form a seal about said seam.

* * * * *